US012349969B2

(12) United States Patent
Angelopoulos et al.

(10) Patent No.: US 12,349,969 B2
(45) Date of Patent: Jul. 8, 2025

(54) BIOMETRIC OCULAR MEASUREMENTS USING DEEP LEARNING

(71) Applicant: Alcon Inc., Fribourg (CH)

(72) Inventors: Robert Dimitri Angelopoulos, San Jose, CA (US); Bryan Stanfill, Mansfield, TX (US)

(73) Assignee: Alcon Inc., Fribourg (CH)

( * ) Notice: Subject to any disclaimer, the term of this patent is extended or adjusted under 35 U.S.C. 154(b) by 860 days.

(21) Appl. No.: 17/501,868

(22) Filed: Oct. 14, 2021

(65) Prior Publication Data
US 2022/0151482 A1  May 19, 2022

Related U.S. Application Data

(60) Provisional application No. 63/113,860, filed on Nov. 14, 2020.

(51) Int. Cl.
*A61B 3/00* (2006.01)
*A61B 3/10* (2006.01)
*G06N 3/08* (2023.01)

(52) U.S. Cl.
CPC .......... *A61B 3/0025* (2013.01); *A61B 3/0058* (2013.01); *A61B 3/102* (2013.01); *G06N 3/08* (2013.01)

(58) Field of Classification Search
CPC ..... A61B 3/0025; A61B 3/0058; A61B 3/102; G06N 3/08; G06N 3/067; G06N 7/046;
(Continued)

(56) References Cited

U.S. PATENT DOCUMENTS

| 2010/0014755 A1* | 1/2010 | Wilson | G06T 7/143 |
| | | | 382/173 |
| 2011/0069279 A1* | 3/2011 | Hacker | A61B 3/102 |
| | | | 351/221 |

(Continued)

FOREIGN PATENT DOCUMENTS

| JP | 2020093076 A | 6/2020 |
| WO | 2020/160839 A1 | 8/2020 |
| WO | 2020172359 A1 | 8/2020 |

OTHER PUBLICATIONS

Huazhu Fu et al: "AGE Challenge: Angle 1-20 Closure Glaucoma Evaluation in Anterior Segment Optical Coherence Tomography", arxiv.org, Cornell University Library, 201 Olin Library Cornell University Ithaca, NY 14853, May 5, 2020 (May 5, 2020), XP081659797.

(Continued)

*Primary Examiner* — Travis S Fissel (57) ABSTRACT

A method for estimating biometric landmark dimensional measurements of a human eye includes, in a possible embodiment, receiving one or more images of the human eye via a host computer. In response to receiving the one or more images, the method includes generating a preliminary set of landmark point locations in the one or more images via the host computer using a deep-learning algorithm, and then refining the preliminary set of landmark point locations using a post-hoc processing routine of the host computer to thereby generate a final set of estimated landmark point locations. Additionally, the biometric landmark dimensional measurements are automatically generated via the host computer using the final set of estimated landmark point locations. A data set is then output that is inclusive of the set of estimated landmark point locations. A host computer that executes instructions from memory to perform the method.

1 Claim, 5 Drawing Sheets

(58) Field of Classification Search
CPC .. G06V 10/143; G06V 10/454; G06V 10/761; G06V 10/764; G06V 10/20; G06V 10/22; G06V 10/23; G06V 10/82; G06V 2201/03; G06V 40/193; G06V 40/19; G01N 29/4481; G06F 2207/4824
USPC .......................................................... 351/206
See application file for complete search history.

(56) References Cited

U.S. PATENT DOCUMENTS

| | | | | |
|---|---|---|---|---|
| 2011/0116041 | A1* | 5/2011 | Hartung | A61B 3/10 351/221 |
| 2018/0109698 | A1* | 4/2018 | Ramsay | A61B 5/4312 |
| 2020/0320401 | A1* | 10/2020 | Jampani | G06N 3/047 |
| 2021/0158525 | A1 | 5/2021 | Iwase et al. | |

OTHER PUBLICATIONS

Wu Hao et al: "3D ultrasound biomicroscopy (3D-UBM) imaging and automated 3D assessment of the iridocorneal angle for glaucoma patients", Progress in Biomedical Optics and Imaging, SPIE—International Society for Optical Engineering, Bellingham, WA, US, vol. 10955, Mar. 15, 2019 (Mar. 15, 2019), pp. 109550U-109550U, XP060118927, ISSN: 1605-7422, DOI: 10.1117/12.2513072 ISBN: 978-1-5106-0027-0.

Tan Hung Pham et al: "Deep Learning Algorithms to Isolate and Quantify the Structures of the Anterior Segment in Optical Coherence Tomography Images", arxiv.org, Cornell University Library, 201 Olin Library Cornell University Ithaca, NY 14853, Sep. 1, 2019 (Sep. 1, 2019), XP081471657.

Huang Bin et al: "Eye landmarks detection via weakly supervised learning", Pattern Recognition, Elsevier, GB, vol. 98, Oct. 9, 2019 (Oct. 9, 2019), XP085886227, ISSN: 0031-3203, DOI: 10.1016/J.PATCOG.2019.107076.

* cited by examiner

BIOMETRIC OCULAR MEASUREMENTS USING DEEP LEARNING

INTRODUCTION

The present disclosure relates to autonomous artificial intelligence-based methods and associated systems for deriving accurate patient biometric measurements, particularly those pertaining to the anatomy of the human eye. Biometry is the process of applying disciplined statistical analysis to a collected set of biological measurements. In an ophthalmological context, biological data includes detailed anatomical measurements of the internal structure of a patient's eye. Patient biometry is therefore an important pre-operative and post-operative component attendant to respective pre-operative and post-operative stages of refractive surgery, intraocular lens selection and implantation, retinal surgery, and other surgical or diagnostic procedures.

Historically, the diagnosis of conditions of the human eye has relied on non-invasive imaging techniques, with ultrasonic biomicroscopy (UBM) and optical coherence tomography (OCT) prevalent in modern medicine. With respect to UBM, this imaging technique is commonly used to image the anterior segment of the eye using ultrasonic energy in a higher frequency range relative to conventional ultrasonic scanning frequencies, e.g., 50-100 MHz. In contrast, OCT is an interferometry procedure in which low-coherence elongated light waves are directed into the eye to image subsurface eye structure such as the macula and optic nerve. Upon collecting UBM, OCT, or other images of the patient's eye, a practitioner will historically mark relevant landmark features in the images and measure the distances therebetween. Inter-pixel distances in the images may be converted to a meaningful scale such as millimeters. The annotated images are thereafter relied upon when evaluating the patient's ocular anatomy, as well as prior to and after performing eye surgery.

SUMMARY

Disclosed herein are non-invasive high-speed evaluation methods and related systems for detecting landmark features in images of a human eye, and for thereafter estimating landmark dimensions between such landmark features. The present teachings rely on deep-learning artificial intelligence (AI) techniques, such as but not necessarily limited to an exemplary convolutional neural network (CNN) as described herein. The present approach operates in an autonomous manner using one or more input images and the AI-informed image processing techniques set forth herein to produce a data set of interocular dimensions in a highly reliable, repeatable, and accurate manner relative to traditional methods of performing patient biometry.

As appreciated in the art, pre-operative surgical plans and post-operative treatment plans require precise knowledge of certain landmark dimensions. Eye surgeries in general may require measurements of the anterior chamber depth, lens thickness, lens diameter, or other key inter-ocular dimensions. Traditional approaches for measuring landmark dimensions include the use of manual box thresholding and hard-coding of dimensional data to predefined images of the patient's eye. Such approaches tend to be highly dependent on the surgeon's unique skill set, and may be suboptimal in terms of accuracy, speed, and repeatability.

Unlike existing techniques, the AI-produced results of the present disclosure are then refined in real-time using classical image processing techniques to reduce noise in the final dimensional estimates, particularly in axial regions of the eye. Distances between refined landmark locations may scaled by image size, and ultimately provide an accurate estimate of measurements of interest without requiring human intervention. A user may optionally interface with a host computer in some embodiment to adjust the deep learning/AI-based predictions so as to customize predictive results to the user's preferences or professional judgment.

In an exemplary embodiment as disclosed herein, a method for estimating biometric landmark dimensional measurements of a human eye includes receiving one or more images of the human eye via a host computer. In response to receiving the one or more images, the method may include generating a preliminary set of landmark point locations in the one or more images via the host computer using a deep-learning algorithm. The method also includes refining the preliminary set of landmark point locations using a post-hoc processing routine of the host computer to thereby generate a final set of estimated landmark point locations. As part of this representative embodiment, the method may include automatically generating the biometric landmark dimensional measurements via the host computer using the final set of estimated landmark point locations, and then outputting a data set inclusive of the set of estimated landmark point locations.

The method may include receiving the one or more images of the human eye from an imaging device in communication with the host computer. In non-limiting implementations, the imaging device may be an ultrasonic biomicroscopy (UBM) device or an optical coherence tomography (OCT) device, without limitation.

The deep-learning algorithm in an exemplary configuration may be a convolutional neural network (CNN). In such an embodiment, generating the preliminary set of landmark point locations may include processing the one or more images via the CNN. Refining the preliminary set of landmark point locations using the post-hoc processing routine may include refining an image pixel intensity, contrast, and/or sharpness level to emphasize at least one landmark point location in the preliminary set of landmark point locations.

In some aspects of the disclosure, automatically generating the biometric landmark dimensional measurements via the host computer using the final set of estimated landmark point locations may include automatically measuring respective linear distances between different estimated landmark point locations in the final set of estimated landmark point locations. The linear distances may correspond to one or more of an anterior chamber depth, a lens diameter, and a lens thickness of the human eye, among other possible intraocular dimensions.

Outputting the data set inclusive of the set of estimated landmark point locations may include displaying and/or printing an annotated image of the human eye inclusive of the linear distances, and/or displaying and/or printing a data table inclusive of the linear distances.

A host computer is also disclosed herein that is configured for estimating biometric landmark dimensional measurements of the eye. The host computer includes memory on which is recorded or stored instructions for a deep-learning algorithm, input/output (I/O) circuitry in communication with an imaging device, and a processor. The imaging device may be an integral part of the host computer in some embodiments. Execution of the instructions by the processor causes the host computer to receive one or more images of the human eye, and in response to receiving the one or more images, to generate a preliminary set of landmark point locations in the one or more images using the deep-learning algorithm. Execution also causes the processor to refine the preliminary set of landmark point locations using a post-hoc processing module to thereby generate a final set of estimated landmark point locations, to automatically generate the biometric landmark dimensional measurements using the final set of estimated landmark point locations, and to output a data set inclusive of the set of estimated landmark point locations.

The above-described features and advantages and other possible features and advantages of the present disclosure will be apparent from the following detailed description of the best modes for carrying out the disclosure when taken in connection with the accompanying drawings.

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through the use of the accompanying drawings. Any dimensions disclosed in the drawings or elsewhere herein are for the purpose of illustration only.

DETAILED DESCRIPTION

Elements of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the present disclosure.

Certain terminology may be used in the following description for the purpose of reference only, and thus are not intended to be limiting. For example, terms such as "above" and "below" refer to directions in the drawings to which reference is made. Terms such as "front," "back," "fore," "aft," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

Figures 1, 2:
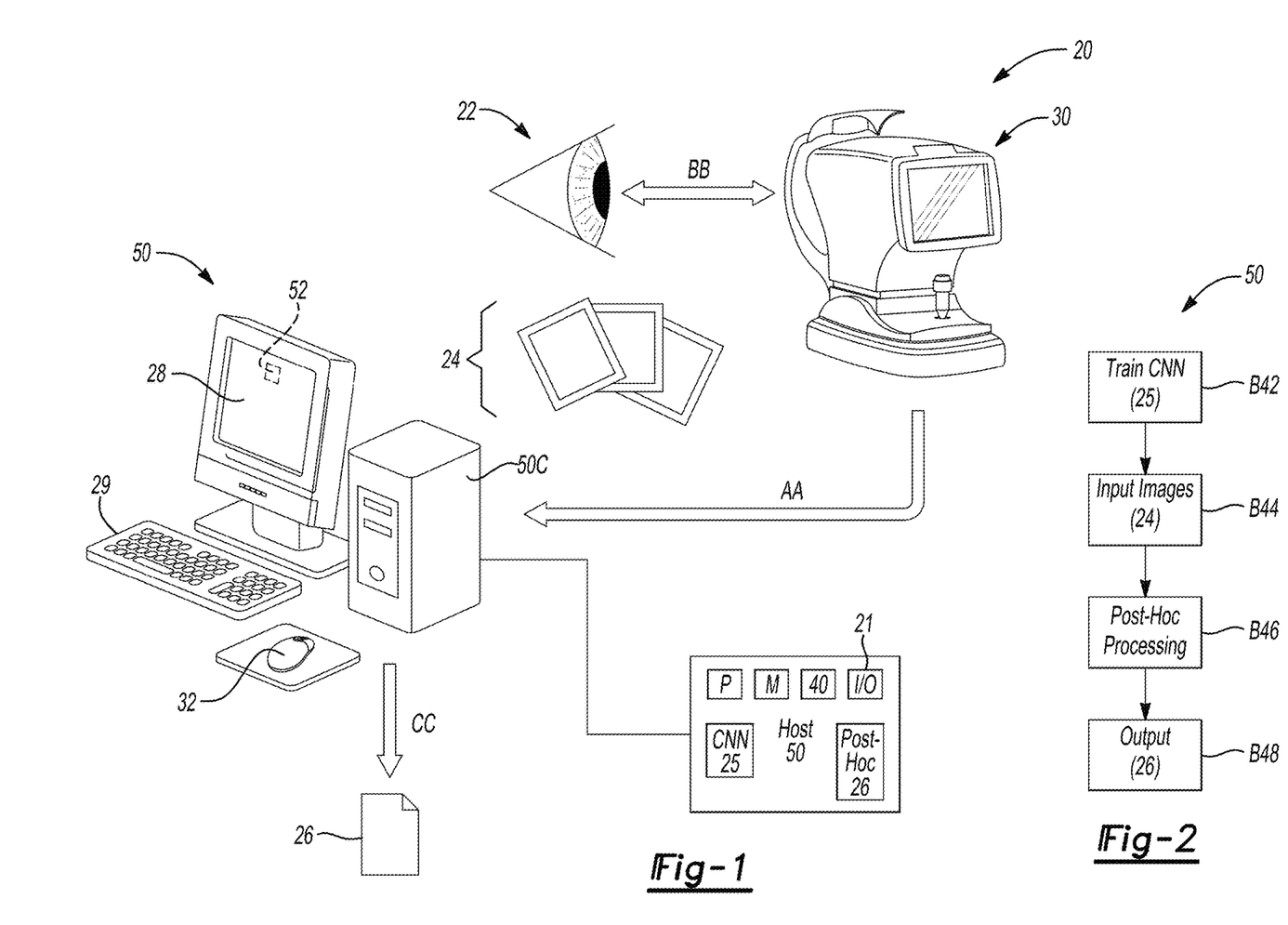
FIG. 1 is a schematic illustration of an autonomous system for deriving measurements from a set of images using the method as set forth herein.
FIG. 2 is a flow chart of the present method according to an exemplary embodiment.

FIG. 1 schematically depicts a system 20 for estimating predetermined dimensions within an eye 22 of a human patient. The system 20 includes an imaging device 30 in wired or remote communication with a host computer (HOST) 50, with the latter configured to perform a deep-learning/artificial intelligence (AI)-based method 40 in cooperation with input data (arrow AA) from the imaging device 30. While the host computer 50 and the imaging device 30 are shown separately in FIG. 1 for illustrative clarity, those skilled in the art will appreciate that the imaging device 30 may be integrated with the host computer 50 in certain embodiments, such that the imaging device 30 forms an integral component or operating element of the host computer 50. An exemplary embodiment of the method 40 is presented in FIG. 2 and described below with reference to FIGS. 3-6, with FIGS. 3-6 depicting representative embodiments of the various inputs, intermediate data, and outputs to/from the host computer 50.

In an exemplary ophthalmological or optical use context as contemplated herein, the imaging device 30 of FIG. 1 is configured to direct and collect energy in a predetermined band of the electromagnetic spectrum toward/into the eye 22, as indicated by arrow BB. The imaging device 30 operates in this manner for the purpose of collecting one or more digital images 24 of the inner anatomy of the eye 22. While other anatomical structure may be imaged within the scope of the disclosure, As understood in the art, the eye 22 works in conjunction with the brain to enable sight. The eye 22 is thus uniquely configured among the body's organs to receive and processes light stimuli to thereby generate electrochemical neural impulses, with such neural impulses ultimately converted by the brain into images and/or colors. In order for the eye 22 to perform its intended biological function, the cornea, lens, ciliary muscles, zonules, vitreous, macula, optic nerve, retina, chambers, and other key anatomical structure of the eye must function effectively. However, due to factors such as injury, age, disease, or genetics a patient may at some point require surgical intervention for vision preservation or enhancement. In such cases, as well as routine examinations, a practitioner may choose to utilize the imaging device 30 to provide a detailed view of the inner anatomy of the eye 22.

Figure 3:
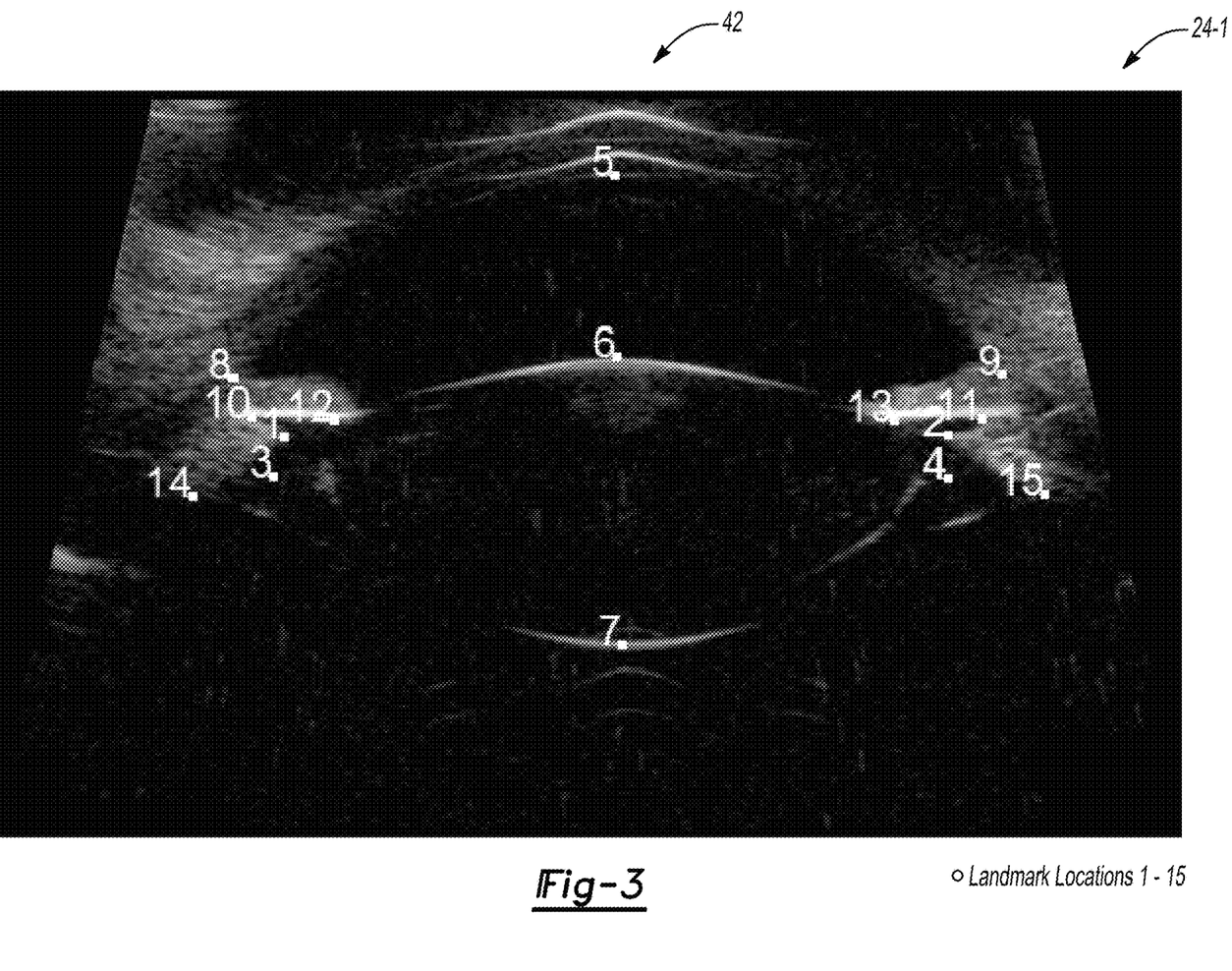
FIG. 3 is a representative image of a human eye depicting various landmark features or points of interest.

To this end, the imaging device 30 shown in FIG. 1 may be variously embodied as an ultrasonic biomicroscopy (UBM) device, an optical coherence tomography (OCT) device, or any other medically relevant embodiment of the imaging device 30. Unlike traditional color images, medical images provided by the imaging device 30 are not clear and unambiguous depictions of the eye 22, but rather are pixelated grayscale images requiring unique collection and analysis expertise. An example UBM image 24-1 is shown in FIG. 3 with added annotations as described below. To rapidly and accurately detect features of interest or landmarks in the images 34 of FIG. 1, therefore, the host computer 50 is programmed in software and equipped in hardware, i.e., configured, to perform the deep learning/AI-based method 40 in response to receipt of the input data AA inclusive of the collected images 24.

The term "deep learning" as used herein and in the general art is a machine learning technique in which one or more computers, in this case the host computer 50, learns features and/or tasks directly from the provided training data. Such data may be in the form of images, text, and/or audio data. Implementations of machine learning may employ neural networks, a typical embodiment of which includes an input layer, several intermediate hidden layers, and an output layer. In deep learning techniques employing neural networks, the neural networks may be multilayered, and may arrange its constituent neurons into several dozen or even several hundred different hidden layers, hierarchical models, and high level filters.

Deep learning in the realm of image processing in particular may incorporate convolutional neural networks or CNNs, with the host computer 50 of FIG. 1 including such a CNN 25 in a possible embodiment as shown. The CNN 25 is configured to receive and process pixel data of a set of training images through the various artificial neurons, with the input images and constituent pixel data automatically classified into particular categories. Thus, a goal of a CNN such as the present CNN, and possibly other deep learning techniques useable within the scope of the disclosure, is to output an approximation of an unknown function via interconnected neurons. Each neuron is selectively activated based on corresponding activation thresholds to pass data to other interconnected neurons. The learning process thus involves applying respective tunable weights within each neuron that are continuously updated based on the exposure of the CNN 25 to additional images 24, and possibly periodically updated using prior classification errors. Ultimately, a nonlinear transformation is applied to a linear combination of the various neural outputs using an activation function to generate the predicted output file 26 as indicated by arrow CC in FIG. 1, e.g., a recognized landmark feature in a given input image 24 or set thereof.

Still referring to FIG. 1, although shown schematically as a unitary device schematic for illustrative simplicity, the host computer 50 may include any number of networked or interconnected computer devices each with sufficient computer-readable media or memory (M) and one or more processors (P). The memory (M) may be in the form of a non-transitory (e.g., tangible) medium that participates in providing data/instructions, which in turn may be read by the processor(s) (P). Memory (M) may take many forms, including but not limited to non-volatile media and volatile media.

While omitted for illustrative simplicity, the host computer 50 may include other hardware or software components such as a high-speed clock, input/output (I/O) circuitry 21 in communication with the imaging device 30 and possibly other hardware components, etc., which may be contained in a tower or other computer housing 50C along with the memory (M) and processor(s) (P). Additionally, the host computer 50 has access to or itself hosts the above-noted CNN 25 and a post-hoc processing module 30 whose operation is described herein below with reference to FIG. 2. To facilitate user interaction with the images 24 when executing the method 40, the host computer 50 may also include various peripheral devices, such as but not limited to a display screen 28, a keyboard 29, a mouse 32, etc. Upon completion of the method 40, the host computer 50 may produce the output file 26 containing the estimated landmark measurements, with an exemplary output file 26 depicted in FIG. 6 and described below.

In some embodiments, the method 40 and underlying functionality of the CNN 25 and the post-hoc processing module 30 may be accessed via an application ("app") tile 52 to launch computer-executable code or instructions. Such code may be written, for example, in JAVA, Markdown, R-languages, or other suitable coding languages. For instance, a user may open the application via the app tile 52 and thereafter point to a folder containing AVI-formatted or other suitable images or videos to be processed. The AVI file may be deconstructed by the host computer 50 into individual discrete images to which deep learning is then applied. The user can then interact with the prediction results, such as by selecting new landmarks on automatically-selected frames, or by selecting a different frame of the video to analyze. The user can also zoom and/or brighten the image to more accurately identify landmark features.

Referring to FIG. 2, the method 40 applies deep learning capabilities to the images 24 to ultimately predict a set of measurements of the eye 22 shown in FIG. 1. Thus, method 40 can be used for estimating certain key biometric landmark dimensional measurements in the human eye 11 of FIG. 1. In a representative embodiment as noted above, deep learning is provided via a deep learning algorithm, e.g., the CNN 25. In such an embodiment, the method 40 commences at a preliminary block B42 with the training of the CNN 25 to correctly identify predetermined landmark locations in the images 24. Training may include, at the onset of block B42, defining a convolutional structure for the CNN 25. With respect to structural definition, block B42 may include defining the number of hidden layers and constituent neurons thereof, inclusive of assigned weights and filters, thresholds, etc., as will be appreciated by those skilled in the art.

Additionally as part of block B42, the method 40 may include compiling a set of training images with pre-marked landmarks of interest. Representative landmarks are depicted at points 1-15 of FIG. 2 by way of example. Parameters of the CNN 25 are learned from the training images using, e.g., optimization algorithm backpropagation or other suitable techniques. Depending on the number of available images for training, either single CNN 25 or several may be used in different implementations. That is, if only a few training images are available for the purpose of training in block B42, then several CNNs 25 will be trained in order to reduce uncertainty in the predictions. Conversely, if thousands of training images are available for training, then a single CNN 25 should suffice for accurately predicting the landmark locations in newly collected images 24.

As will be appreciated, and as summarized separately above, a given CNN 25 includes a convolutional layer which receives a set of inputs, in this instance the training images at block B42. Each artificial neuron of the CNN 25 may be represented as a set of input values, each with associated weights, along with a function that sums the weights and maps the results to a predicted output. Artificial neurons in the form of filters or kernels are then used to perform element-wise multiplication functions by moving over the input images and multiplying values in the filter with the image pixel values. A feature map is generated in this manner.

Thus, the convolutional layer of the CNN 25 used as part of method 40 may utilizes filters in the form of a matrix to detect the presence or absence of specific features or patterns in the training images of block B42, with the same process occurring later in the execution of method 40. Multiple hidden layers, e.g., more convolutional layers or more pooling layers, may receive the feature map and thereafter process the feature map through additional filters. The predicted results then pass through an output layer as a predicted value, which in the present method 40 includes one, some, or all of the indicated landmarks 1-15 shown in the representative image 24-1 of FIG. 3. In this manner, the CNN 25 is able to extract high-level landmark features such as corners, edges, and curvatures from a set of input images.

In effect, block B42 allows of the CNN 25 to be trained by comparing its classification of a given set of training images with predetermined correct baseline classifications, i.e., validated reference images. Errors from initial and subsequent classification iterations may be fed back into the CNN 25 and used to modify the various neural weights and filters over as many iterations as are needed to properly train the CNN 25. The method 40 then proceeds to block B44 once the CNN 25 has been trained.

Block B44 entails receiving the one or more images 34 of the eye 22 via the host computer 50, i.e., effectively inputting the collected images 24 of FIG. 1 into the host computer 50 and the CNN 25 or another application-suitable deep-learning algorithm thereof. Some embodiments of block B44 may include collecting the one or more images 24 as using the imaging device 30, and then digitally transmitting the collected images 24 to the host computer 50.

Referring briefly to FIG. 3, a baseline image 24-1 of the eye 22 of FIG. 1 is shown in the form of a UBM image overlaid, solely for the purpose of illustration, with representative landmark points nominally labeled 1-15. Visible at the top of FIG. 3 are corneal echoes 42 having a recognizable pattern that serves to help locate and identify the remaining imaged structure of the eye 22. Key landmark points of interest would be recognized by an ophthalmologist or others skilled in the art within the image 24-1 as follows:

| Landmark Points | Dimension |
| --- | --- |
| (5, 6) | Anterior Chamber Depth 5 ←→ 6 |
| (1, 2) | Ciliary Process Diameter 1 ←→ 2 |
| (8, 9) | Interior Chamber Depth 8 ←→ 9 |
| (6, 7) | Lens Thickness 6 ←→ 7 |
| (3, 4) | Lens Diameter 3 ←→ 4 |
| (10, 11) | Sulcus-to-Sulcus 10 ←→ 11 |

Figure 4:
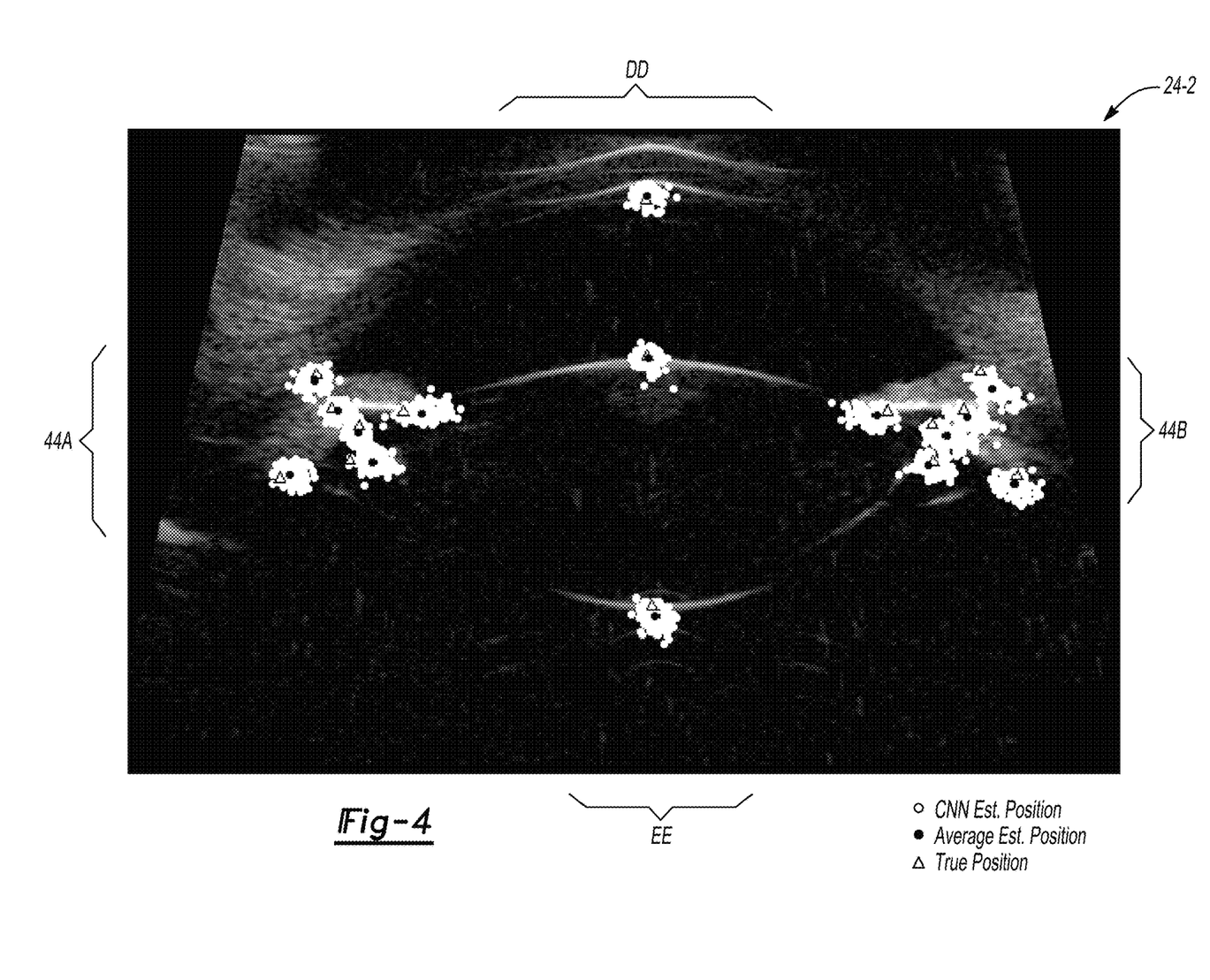
FIG. 4 is the representative image of FIG. 3 after processing by an exemplary convolutional neural network in accordance with the present disclosure.

As part of block B44, response to receiving the one or more images 24 the host computer 50 may generate a preliminary set of landmark point locations in the images 24 using a deep-learning algorithm, in this example the CNN 25. The CNN 25, as part of block B44, may estimate the distribution and locations of the above-noted landmark points 1-15 by processing multiple images 24 similar to the image 24-1 through the trained CNN 25. FIG. 4 depicts representative initial deep learning results as an image 24-2, with CNN 25-provided estimated positions shown as white circle clusters in regions 44A and 44B, the average of which is depicted, for a given landmark point, as a black circle in the centers of such regions.

Thus, FIG. 4 is representative of results in which the CNN 25 processes several different images 24 of the eye 22, e.g., by separating a video stream taken over a predetermined sampling interval into multiple temporally-related discrete images 24. Processing of each image 24 may provide a slightly different predicted landmark point, with the result appearing as the clusters in regions 44A and 44B as shown. Also indicated in FIG. 4 via triangles for reference are the true positions of each of the landmark points 1-15 shown in FIG. 3. Thus, block B44 may include calculating the mode or average of each set of landmark location estimates to provide a single estimated landmark point location. The method 40 then proceeds to block B46.

Figure 5:
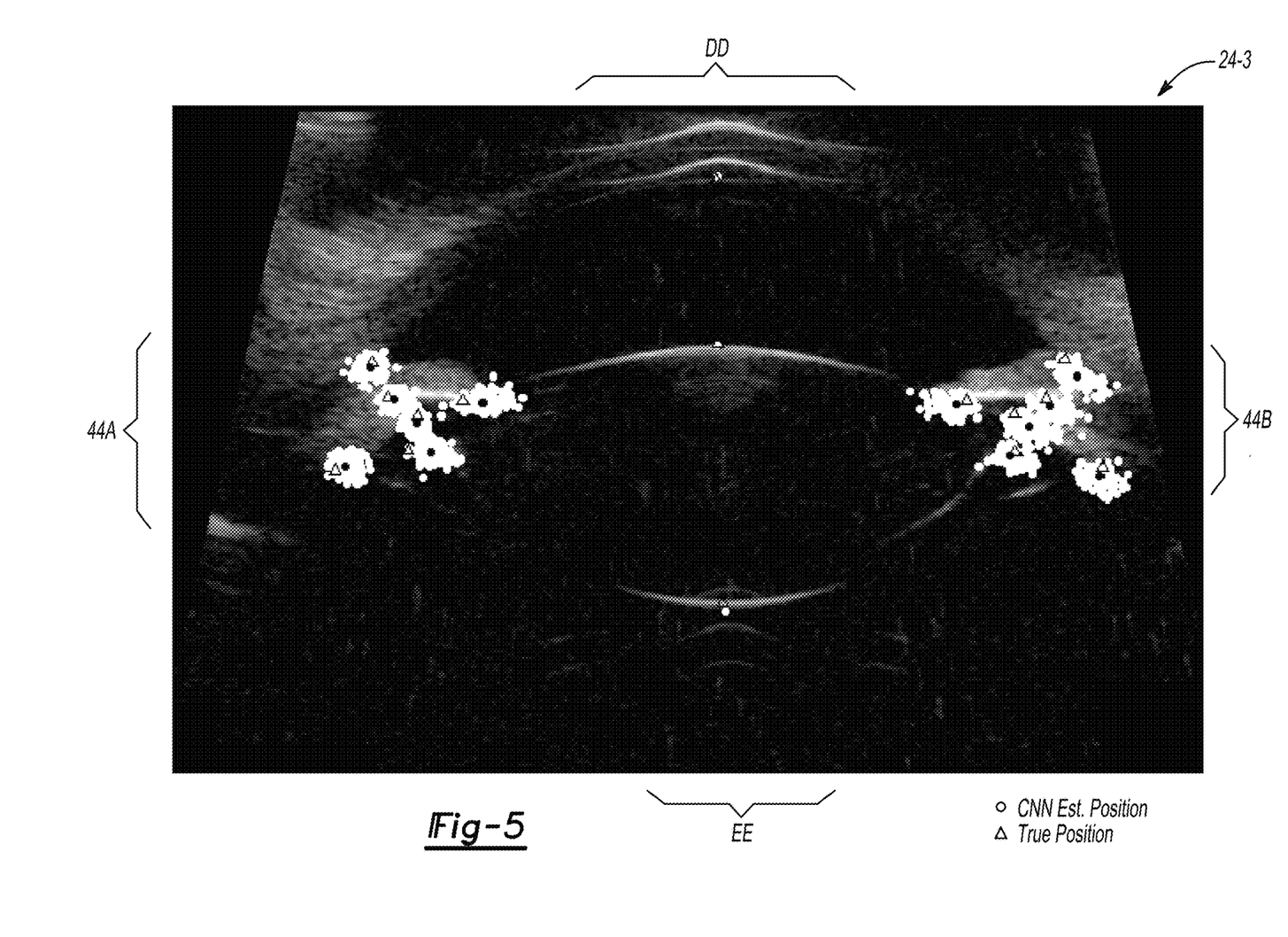
FIG. 5 is the representative image of FIGS. 3 and 4 depicting adjusted landmark locations after post-hoc processing.

Block B46 includes refining the preliminary set of landmark point locations using the post-hoc processing module 30, which in turn executes a predetermined post-hoc processing routine to thereby generate a final set of estimated landmark point locations. Representative techniques for post-hoc processing include refining the image pixel intensity, contrast, sharpness, etc., to bring out details of one or more particular landmark points of interest. For instance, FIG. 5 depicts a representative result image 24-2 of the final set of estimated landmark point locations made possible using such post-hoc processing, after filtering out noise and further refining the results in a particular center region between brackets DD and EE, which encompasses the landmark points 5, 6, and 7 of FIG. 3 that are of particular importance when deriving anterior chamber depth and lens thickness. Thus, the predicted landmark positions or locations from the CNN 25 may be adjusted post-hoc in block B46 to incorporate additional image information into the predictions. As post-hoc processing occurs on a flat two-dimensional image, corresponding XY coordinates are available for each of the landmark points of interest. The method 40 proceeds to block B48 of FIG. 2.

At block B48, the method 40 of FIG. 2 concludes by automatically generating biometric landmark dimensional measurements using the final set of estimated landmark point locations, with determination of such measurements or dimensions performed by the host computer 50 of FIG. 1, and with the identifies of such measurements possibly pre-programmed into memory (M) of the host computer 50. For example, the host computer 50 may automatically calculate linear distances between any of the representative landmark points 1-15 of FIG. 3 whose positions or locations have been predicted by operation of the CNN 25 and thereafter refined by the post-hoc processing module 30. A given landmark dimension may be determined by scaling the distance between any two such located landmarks by a pixel resolution of the image 24 in question.

Figure 6:
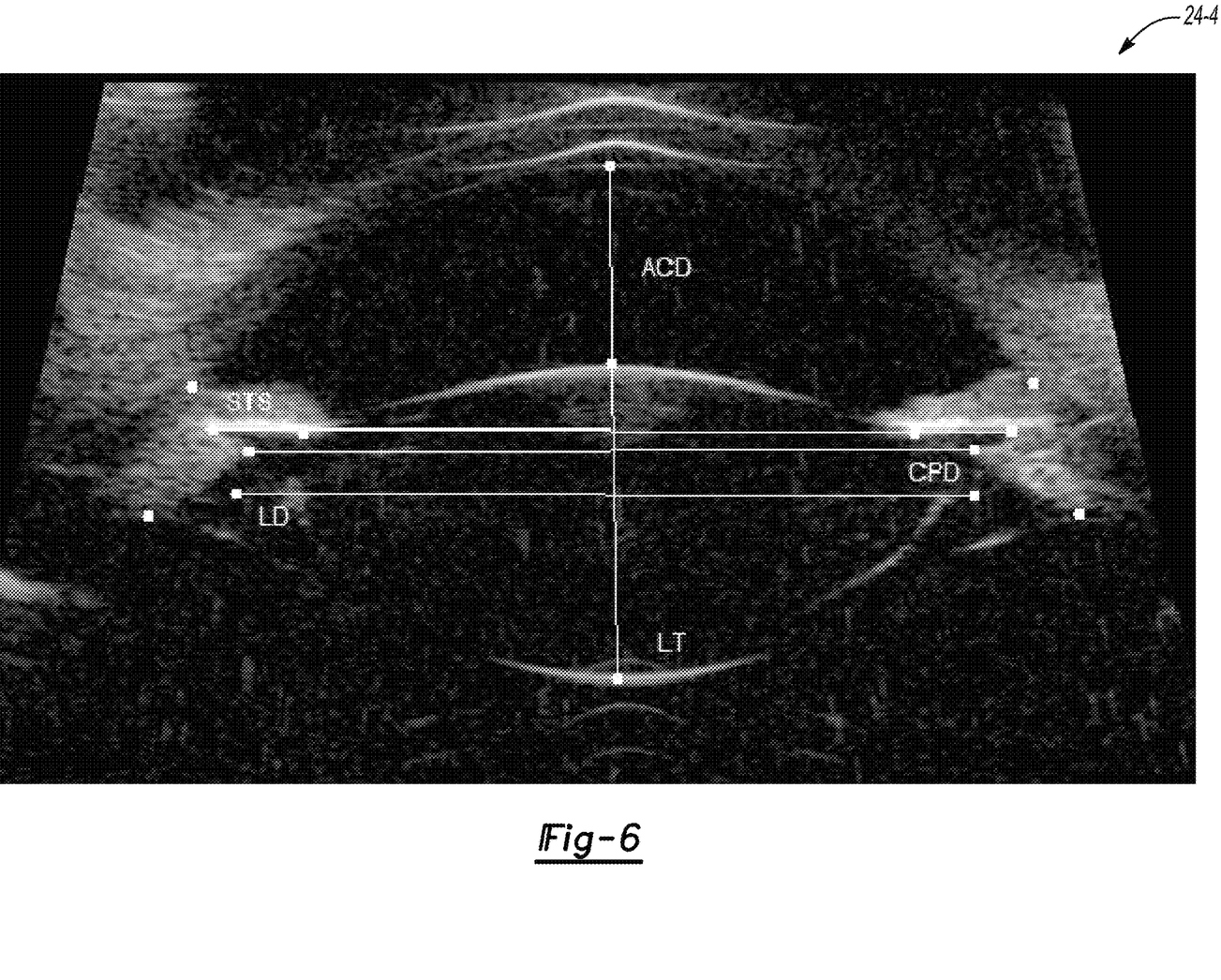
FIG. 6 is the representative image of FIG. 5 after automated dimensional annotation in accordance with the present disclosure.

As part of block B48, the host computer 50 of FIG. 1 may generate the output file 26 inclusive of the estimated landmark measurements, with block B48 thus encompassing outputting a data set inclusive of the set of estimated landmark point locations, e.g., by displaying a data table on the display screen 28 and/or printing a data table inclusive of the linear distances. A user may adjust any of the landmark locations, in which case a user-specified measurement may appear in a separate column of such a table. An exemplary embodiment of optional image content of such an output file 26 is represented as annotated image 24-4 of FIG. 6, with various landmark dimensions delineated and labeled as follows:

ACD=anterior chamber depth
STS=Sulcus-to-sulcus distance
CPD=Ciliary process diameter
LD=Lens diameter
LT=Lens thickness Such representative dimensions are commonly used for intraocular lens power calculations, refractive surgery customization, and retinal disease diagnosis and surgery, among other procedures.

The present solution enabled by method 40 and the disclosed CNN 25 thus allows for rapid initial identification of landmark points in the eye 22 shown in FIG. 1. The initial estimated landmark positions are then refined via the post-hoc processing module 30 using classical image processing techniques. Distances between the refined landmark locations forms an estimate of the true measurement, with a mode of multiple landmark position estimates possibly used as the final measurement.

Using a lens as an example anatomical structure to be identified in a raw image 24, the CNN 25 described above is not instructed as to where the lens is in the image 24, or indeed if a lens even appears in the image 24. Instead, the CNN 25 is taught the characteristics of the lens and then, during subsequent operation, the CNN 25 is tasked with locating similar "lens-like" characteristics in the image(s) 24. The method 40 thus replaces human-specified regions of interest in a given image of the eye 22 of FIG. 1 when deriving accurate biometric measurements.

The present solutions may be completely automated or, in other embodiments, may preserve a limited role for the surgeon or practitioner, e.g., during post-hoc processing. In either case, execution of the method 40 greatly improves the accuracy, repeatability, and reliability of ocular measurements relative to existing methods. Further, post-hoc refinement of the estimates reduces noise in the final estimates, particularly in the axial regions of the eye 22. Useful measurements are predicted regardless of the number of images 24 that are provided to the CNN 25, with overall improved predictive accuracy provided via a greater number of images 24.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims.

Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed:

1. A method for estimating biometric landmark dimensional measurements of a human eye, the method comprising:
receiving one or more ultrasonic images of the human eye via a host computer;
in response to receiving the one or more ultrasonic images, generating a preliminary set of landmark point locations in the one or more images via the host computer using a convolution neural network (CNN);
refining an image pixel intensity, contrast, and/or sharpness level of the preliminary set of landmark point locations to emphasize at least one landmark point location, using a post-hoc processing routine of the host computer, and to thereby generate a final set of estimated landmark point locations;
automatically measuring respective linear distances between different estimated landmark point locations in the final set of estimated landmark point locations to thereby generate the biometric landmark dimensional measurements, including an anterior chamber depth, a lens diameter, and/or a lens thickness of the human eye; and
outputting an annotated image and a data table inclusive of the linear distances.

* * * * *